United States Patent [19]

McCollum

[11] Patent Number: 4,550,011
[45] Date of Patent: Oct. 29, 1985

[54] SAMPLE FLOW CELL FOR AUTOMATIC HALOGEN AND PH CONTROL FOR WATER RESERVOIRS

[76] Inventor: Roy L. McCollum, 14210 Broadgreen, Houston, Tex. 77079

[21] Appl. No.: 510,415

[22] Filed: Jul. 1, 1983

[51] Int. Cl.$^4$ .................................. G01N 27/38
[52] U.S. Cl. .................................. 422/68; 204/1 T; 204/409; 204/433; 210/94; 210/96.1; 210/140; 210/169; 324/65 P
[58] Field of Search ............... 204/1 B, 1 H, 1 T, 400, 204/409, 433; 210/739, 743, 746, 754, 94, 96.1, 139, 140, 169; 324/65 P, 65 CR, 61 P, 438; 422/68, 75, 76

[56] References Cited

U.S. PATENT DOCUMENTS

| | | | |
|---|---|---|---|
| 3,178,901 | 4/1965 | Blackett | 324/65 CR |
| 3,298,934 | 1/1967 | Angeleri | 422/68 |
| 3,714,039 | 1/1973 | Lancy et al. | 210/743 |
| 4,016,078 | 4/1977 | Severin | 210/139 |
| 4,033,871 | 7/1977 | Wall | 210/756 |
| 4,064,047 | 12/1977 | Bernreiter et al. | 210/96.1 |
| 4,126,550 | 11/1978 | Doerschlag | 210/743 |
| 4,129,479 | 12/1978 | Morrow | 204/409 |
| 4,435,291 | 3/1984 | Malsko | 210/739 |

Primary Examiner—Peter Hruskoci
Attorney, Agent, or Firm—Jack W. Hayden

[57] ABSTRACT

A cylindrical closed housing formed of clear material provides a test flow cell for monitoring the halogen and pH level in a flowing liquid stream. The cylindrical housing includes a circumferential, longitudinally extending side surface with front and back end surfaces secured to the circumferential cylindrical surface to form the closed, hollow housing test cell. The housing has a first inlet opening at one side for the liquid stream; an outlet opening for the liquid stream at the top of the housing and a second inlet opening for acid at the bottom of the housing. A pair of additional openings, one on each side of the outlet opening receives and positions electronic sensing probes diagonally within the test flow cell; the probes terminate between the top outlet and bottom second inlet openings and opposite the first inlet side opening.

A controller includes circuitry which enables the halogen and pH levels desired in a reservoir of water to be preset. The sensing probes measure the actual halogen and pH levels in the reservoir water, and the actual and preset levels are continuously compared by a comparator circuit in the controller. When the measured halogen level is below the set halogen level, additional halogen is injected in the reservoir water. A timer provides a timed electric signal at a predetermined interval to actuate pump means to inject muriatic acid during the timed signal period into the reservoir water if the measured pH is higher than the preset pH level of the reservoir water.

1 Claim, 5 Drawing Figures

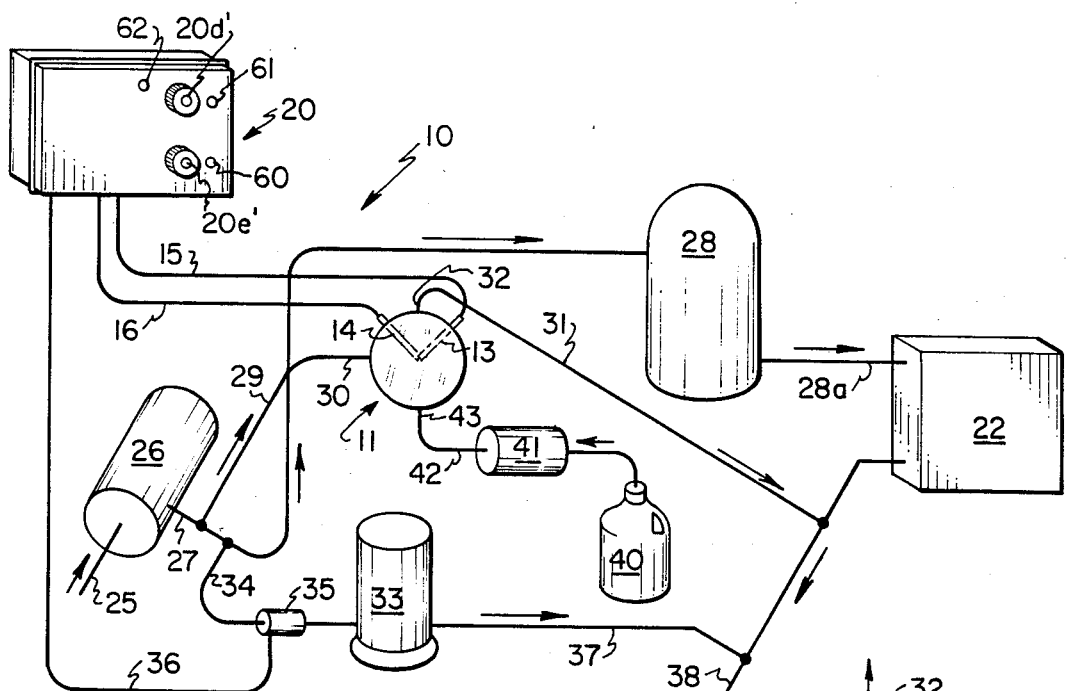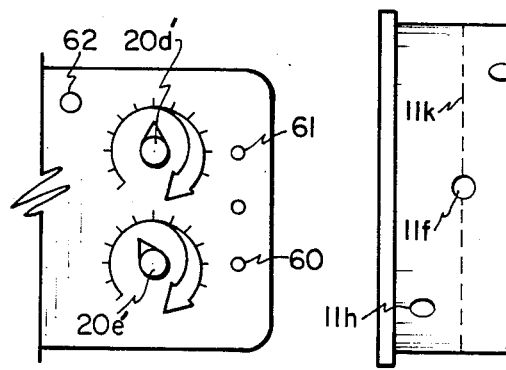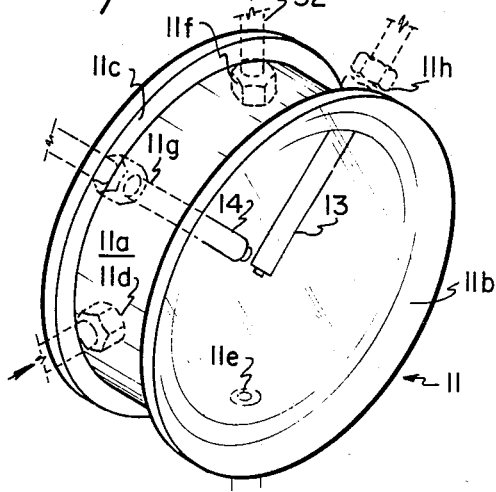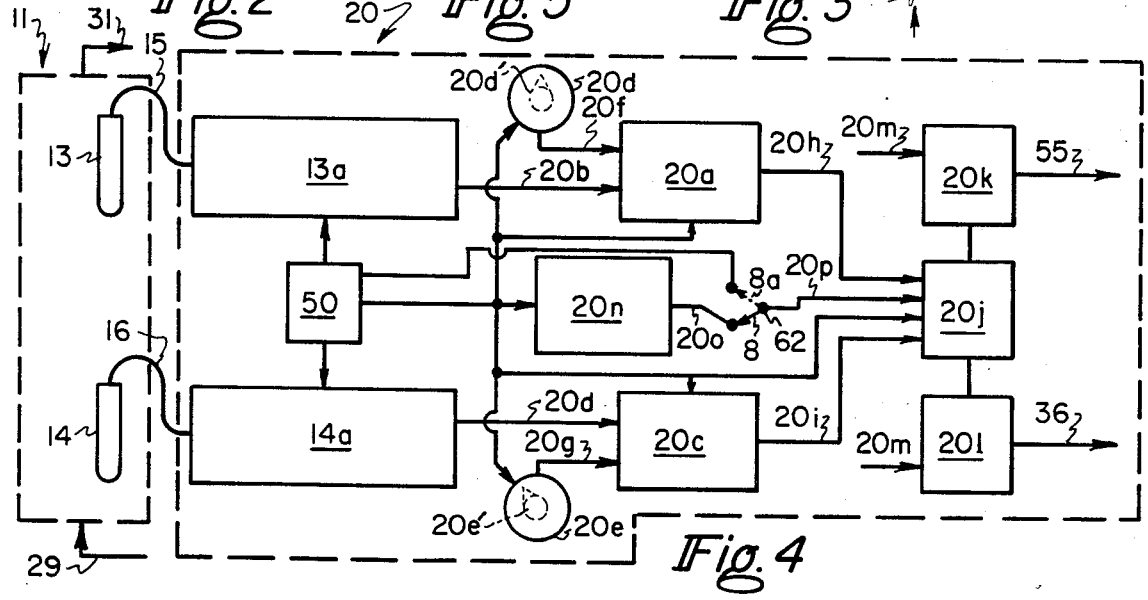
Fig. 1
Fig. 2
Fig. 5
Fig. 3
Fig. 4

SAMPLE FLOW CELL FOR AUTOMATIC HALOGEN AND PH CONTROL FOR WATER RESERVOIRS

SUMMARY OF THE INVENTION

Determining the halogen and pH level (negative logarithm of the hydrogen ion concentration) of a reservoir of water such as swimming pool water is notoriously old. Similarly, comparing it with a predetermined desired level of pH and halogen to be maintained in the swimming pool is old. Injecting muriatic acid and additional halogen into the swimming pool water when the measured level varies from the desired set level is also old in the art.

However, previous arrangements with which the applicants are familiar tend to overcorrect the pH by feeding acid into the pool or reservoir until the pH measurement indicates the proper pH at the location of the pH probe. The dilution process in the pool is incomplete at this point, and the pH will eventually be significantly lower when all the acid is uniformly mixed with the pool water. The present invention overcomes this problem by feeding acid for only a set period of time, such as two minutes, out of a predetermined interval, such as each hour interval. The remaining time, such as 58 minutes, allows for complete mixing of the acid and thus prevents overcorrection.

Another problem with prior art arrangements is that the sensing probes have been inserted in such a manner that there may be substantial turbulence, or air which may cause interferences resulting in an improper reading.

Further, calcification and mineral buildup on the electronic sensing probes require periodic acid cleansing to keep them accurate. In these instances, this requires that the probes be removed at intervals, such as every two to four weeks and then washed with muriatic acid.

Also, calibration or setting prior equipment is somewhat complicated and difficult, usually requiring a signal generator.

The present invention overcomes the above problems in that it provides a sample cell which receives a continuous flow of water from a reservoir in a manner so that turbulence is substantially decreased, if not completely eliminated to enable a more accurate measurement by the probes. Further, the sample cell is formed of clear material so that the probes may be visually inspected, and the sensing probes are positioned in the sample cell relative to the acid inlet and the fluid outlet from the housing so that the acid injected into the sample cell contacts the probes which cleans and maintains the sensing probes clean during use. Timed periodic injection of the acid substantially reduces, if not completely eliminates, the problem of acid overfeed, and the present invention is maintained set or calibrated for use.

The present invention provides an arrangement for monitoring and regulating the introduction of a water purification substance and a pH compensation substance into a reservoir of water in a manner so as not to overfeed the substances and maintain the substances at a desired level.

Other objects and advantages of the present invention will become more readily apparent from a consideration of the following description and drawings.

BRIEF DESCRIPTION OF THE DRAWINGS

FIG. 1 is a view illustrating a diagrammatic layout of the present invention as it is applied to use wherein the water reservoir is a pool;

FIG. 2 is an enlarged view of the right hand side of a portion of the controller shown in FIG. 1;

FIG. 3 is a perspective view of the sample cell;

FIG. 4 is a schematic illustration of the electronic controller components and a diagrammatic representation of their relationship with the controller; and FIG. 5 is a view diagrammatically illustrating the preferred physical relationship of the inlets in the housing for the probes in relation to the top outlet opening.

BRIEF DESCRIPTION OF THE PREFERRED EMBODIMENT

The present invention may be employed with any reservoir of water in which it is desired to monitor and control the pH and/or halogen content. By way of example only, the invention will be described in detail in relation to a swimming pool, but this is for purposes of illustration only and is not intended by way of limitation.

Attention is first directed to FIG. 1 of the drawings wherein the arrangement of the present invention is illustrated generally by the numeral 10. The sample flow cell is referred to generally at 11 with the sensing probes 13 and 14 positioned diagonally therein. The sensing probes 13 and 14 are connected by suitable electrical conductor means 15 and 16 with the electronic controller represented generally at 20. Flow from the swimming pool is conducted through the line 25 to the pump 26 and is discharged through the conduit 27 to flow to the filter 28. A conduit 29 is provided downstream of the pump 26 and connects with the discharge conduit 27 for supplying a continuous flow sample of swimming pool water to the sample cell 11. It will be noted that the conduit 29 is connected into the side of the sample cell as indicated at 30 and as will be described in greater detail hereinafter. The discharge conduit from the sample cell is represented at 31 and is shown as being connected into the top of the sample cell as represented at 32. Conduits 29 and 31 are diagrammatically represented in FIG. 4.

A halogen source, such as bromine or chlorine, if represented at 33 and is connected by the conduit 34 into the discharge line 27 downstream of the conduit 29. Suitable solenoid actuated valve means 35 is connected by the electrical conduit 36 to the controller 20 for actuation of the solenoid valve 35 to open conduit 34 so that water may flow from the discharge line 27 through the conduit 34, the solenoid valve 35, through the halogenator 33 to pick up the halogen and then to be discharged out the line 37 from the halogenator into the return line 38 back to the swimming pool.

A muriatic acid source is represented at 40 and is connected to a pump 41 which is electronically connected by the conduit 55 (not shown in FIG. 1) to the controller 20 for pumping acid into the discharge line 42 of pump 41 and into the bottom of the sample cell 11 as represented at 43. It will be noted that the discharge 31 from the sample cell is connected into the discharge line 38 for flow back to the swimming pool.

The discharge from the filter 28 passes through the discharge 28a to the heater 22 and then back through the discharge line 38 to the swimming pool. As shown, it will be noted that the acid and chlorine or bromine are preferably added to the return line 38 in a manner to bypass the filter 28 and heater 22.

The sample cell 11 of the present invention is illustrated in greater detail in FIG. 3 of the drawings and, as will be seen, is a cylindrical, hollow, closed housing formed of clear material such as plastic or the like. The circumferential side surface 11a of cell 11 extends longitudinally a desired extent and secured therewith are the front and back end surfaces 11b and 11c, respectively, which overlap and are secured to the circumferential longitudinally extending portion 11a by any suitable means such as bolts, glue or the like. If desired, the sample cell may be formed by molding so that the side, front and back surfaces form a unitary arrangement. This arrangement forms the cylindrical, hollow, closed housing, and it will be noted that the first inlet opening 11d is on one side of the cylindrical housing side surface 11a with the outlet opening 11f being on the top of the housing side surface 11a and the second inlet opening 11e being at the bottom of the housing side surface 11a, preferably in diametrically opposed relationship to the outlet opening as shown.

A pair of additional openings is provided in the housing and spaced to position the sensing probes 13 and 14 in a diagonal relationship within the sample cell and terminating at a position between the second inlet 11e and the outlet opening 11f at the top of the housing. The electronic sensing probes 13 and 14 are further positioned so that they are opposite the inlet opening as shown.

As demonstrated in FIG. 5, the outlet opening 11f is between the pair of additional openings 11g and 11h, and the openings 11g, 11h are offset along the longitudinal axis of the cylindrical cell 11 from each other.

This is better demonstrated by referring to FIG. 5 which shows the transverse plane represented by dotted line 11k through cylindrical housing 11 at top outlet 11f. The openings 11g, 11h are offset on opposite sides of the plane represented at 11k and are in circumferential spaced relation to each other as shown.

Preferably, the sensing probes 13 and 14 terminate about midway of the sample cell, or generally in the central portion thereof as shown which will place them approximately midway between the second inlet 11e and the outlet 11f as well as being opposite and spaced from the flow water inlet 11d. Preferably, the sensing probes are also substantially or generally aligned with the flow inlet 11d as well as the outlet 11f and the second inlet 11e.

The electronic portion of the apparatus for automatically controlling the halogen (chlorine or bromine) and muriatic acid level in swimming pool water of the present invention is shown schematically in greater detail in FIG. 4 of the drawings. The components of the controller 20 are represented within the dotted line in FIG. 4. The sample cell is represented at 11 with the probes 13 and 14 therein. As previously noted, the probes 13 and 14 are connected electronically to the controller 20 as represented in FIG. 1 and 4 by the electrical conduits 15 and 16 which connect pH measurement probe 13 with amplifier 13a and which connect halogen measurement probe 14 with amplifier 14a, respectively. Comparing means include and electronic analog comparator circuit substantially represented at 20a which is electrically coupled by conduit 20b to the amplifier 13a, and an analog comparator circuit schematically represented at 20c which is connected by the electric conductor 20d to the amplifier 14a.

A pH set control circuit is represented at 20d and a halogen, such as chlorine or bromine, set point control circuit is schematically represented at 20e, each of which is electrically connected by 20f and 20g, respectively, to its analog comparator circuit 20a and 20c and each of which provides to its respective comparator circuit 20a, 20c an electric signal functionally related, respectively, to the desired pH level and purification substance content in the water. The analog comparator circuits 20a and 20c for the pH and chlorine, respectively, are in turn connected by the electrical conduits 20h and 20i to a control circuit 20j. The control circuit is in turn connected to a power relay 20k for actuating the pump 41 for supplying acid to the sample cell 11 and the power relay 20l for supplying power to the solenoid valve 35 whereby chlorine or bromine, whichever is used, may be added to the swimming pool water through conduits 37.

Timing means, including timer counter circuit 20n provides an enabling electrical signal for a set or fixed period of time at repeated predetermined spaced time intervals by means of the conduits 20o and 20p to the control circuit 20j, whereby the acid pump 41 is actuated during the timed period at the predetermined intervals when the circuitry indicates that the pH of the swimming pool water should be lowered to match the predetermined set point in circuit 20d, as will be explained. All the foregoing circuits comprise standard electronic components, and it is believed unnecessary to provide any detailed description as to the circuit details as such is well known to those skilled in the art.

Suitable power is provided for the relays 20k and 20l as indicated at 20m, and a suitable power source 50 is provided for the components of controller 20. While the power source 50 is shown schematically within controller 20, it can be appreciated that preferably it will be external of controller 20 for supplying power thereto and all components which require power.

To further amplify and describe the operation of the present invention, it will be assumed that it is connected as shown in the drawings. Water from the swimming pool is conducted through the pipe 25 to the pump 26 and discharged through the pump discharge line 27. A portion of this flowing swimming pool water from line 27 flows continuously through line 29 into the inlet opening on the side of the sample cell 11. The outlet from the sample cell 11 is at the top of the sample cell, as shown in the drawings, and thus the sample cell 11 is maintained full by the water being controlled at all times. This tends to decrease the chances of the presence of air within the cell 11 which might interfere with the proper operation of the sensing probes 13 and 14. The probes 13 and 14 continuously monitor and determine the pH of the water flowing in the conduit 27 and through the sample cell 11 as well as the oxidation reduction potential thereof as a measure of the free chlorine or halogen present in the water in the line 27 from the swimming pool pump 26. The amplifiers 13a, 14a, respectively, transmit these two measurements as separate electrial signals to the pH and halogen comparator circuits 20a and 20c continuously. These two separate signals are, respectively, functionally related to the pH level and halogen content of the water and the comparator circuits 20a and 20c continuously electronically compare the measured pH and the measured free chlorine content of the water with the desired level in the reservoir or swimming pool. The desired level of pH and halogen is that which has been set or predetermined in the comparator circuits 20a, 20c, respectively, by the pH set point control circuit 20d and chlorine set point control circuit 20e. The set or predetermined pH or halogen level in circuits 20a, 20c is controlled by manually turning the control knobs 20d' and 20e' on the face of the controller 20 as illustrated in FIGS. 1 and 2 as will be described.

The pH level and the chlorine or bromine level in the flow stream 27 are monitored continuously by the present invention, and such level is compared continuously with the desired level set manually by knobs 20d', 20e' in the set point controls 20d and 20e.

Comparator circuit 20a provides a first electrical signal when the pH level, as determined by the comparator circuit 20a, of the reservoir water is higher than that desired and higher than that indicated in set point control circuit 20d which is transmitted to comparator circuit 20a. This electrical signal is supplied to control circuit 20j to actuate acid pump 41 as will be described.

When the level of halogen, such chlorine or bromine, as determined by the comparator circuit 20c is below that desired and below that indicated in the set point control circuit 20e and transmitted to comparator circuit 20c, the comparator circuit 20c provides a second electrical signal which acts through conduit 20i to actuate the control circuit 20l which in turn actuates power relay 20l so that power is supplied through conduit 36 to the solenoid valve 35 to permit water to flow from the line 27 through the halogenator 33, such as a chlorinator or brominator, and absorb such halogen into the water which is then discharged then through the conduit 37 into the return line 38 going back to the swimming pool. The halogenator 33 is of any suitable standard type. For example, it may contain chlorine sticks or tablets which dissolve when valve 35 opens to permit water to flow through conduit 34 and through the bottom of halogenator 33.

In order to avoid overfeeding of acid, the portion of the control circuit 20j which controls the flow of power to operate acid pump 41 is permitted to be actuated only at predetermined intervals. By way of example, the time circuit 20n is arranged so that is conducts a signal to control circuit 20j once every hour for two minutes. If during this two minute interval the comparator circuit 20a by comparing the set level of pH desired from the set point control circuit 20d with the pH measured by the probe 13 determines that additional acid is required to maintain the pH at the level of that as set by pH set point control circuit 20d, then during the period of time that the timer circuit 20n permits the control circuit 20j to be actuated for operating the acid pump 41, acid will flow into the sample cell 11 from the source 40 by means of the pump 41 and through conduit 42. It should be noted that even though the pH of the water flowing in conduit 27 is being monitored continuously by the present invention, acid is not added to the water except at the periodic interval when the timer circuit 20n permits the control circuit 20j to be activated for acid addition. During the remaining inactivated interval, the timer circuit 20n maintains the portion of the control circuit 20j which controls relay 20k deactivated. This enables the acid added during the timed interval, such as two minutes, to mix with the pool water for a substantial period of time such as, for example, one hour, before the portion of the control circuit 20j is again activated to permit additional acid to be added, if necessary. If the pH comparator circuit 20a indicates that no acid should be added, then none is added during the interval that the timer circuit provides an enabling signal to control circuit 20j.

Another advantage of the present invention is the ease with which it may be calibrated. For example, the normal method of setting or calibrating other systems on the market is with the signal generator which transmits the ideal signal from the electrodes into the unit so then the unit can be calibrated to a specific pH number or halogen PPM or content; however, these numbers then have to be adjusted to compensate for the interferences which could be affected by temperature, alkalinity level and the like. They can also be greatly affected by mineral content of the water from one part of the country to the other.

To calibrate the present invention, all that is necessary is for the pool owner to take a simple test kit and test the swimming pool water to determine the chlorine and pH level. If the pH and halogen content is not at the desired level, acid and halogen are manually added, and then the pH and halogen are measured again after a suitable period. When the test kit for pH and chlorine or bromine shows the desired pH and halogen level in the pool, the halogen set point circuit 20e and the pH set point circuit 20d are adjusted to input into their respective comparator circuits 20c and 20a the desired halogen level and pH level so that the comparator circuits 20c and 20a may eletronically compare the actual measured halogen and pH levels in the swimming pool water with desired levels and effect the addition of acid and halogen if necessary. For example, the chlorine or bromine set point circuit 20e which introduces the desired halogen level into the halogen comparator circuit 20c is set at this desired halogen level for the pool water by turning the dial 20e' until the small light at 60 on the front panel of controller 20 comes on, and this automatically sets the halogen comparator circuit 20e at the desired level of chlorine in the pool. The light 60 is electronically connected into the set point circuit 20e in a manner well known to those skilled in the art. Similarly, the pH set point control circuit 20d is employed to input to the pH comparator circuit 20a the desired pH level to be maintained by the present invention in the swimming pool flow stream 27. When the desired pH level in the pool is attained, the dial 2d' is turned until the small light 61 on the front panel of controller 60 goes out. This will then set the pH comparator circuit 20a so that the measured pH level is continuously compared with the desired pH level in the pool. light 61 is electronically connected into the pH set point circuit 20d in a manner well known to those skilled in the art.

If the pool owner desires to change (raise or lower) the pH or chlorine level in the pool, the knobs or dials 20d', 20e' can be adjusted accordingly and then the water tested in several days to verify that the desired level has been attained.

It should be noted as the pH set point circuit 20d is set by turning dial 20d', it is necessary to push in on the pH set switch 62 on the front panel of controller 20 which deactivates the timer circuit 20n and moves the movable contact 8 to the position indicated in dotted line at 8a so that the enabling signal derived from the power supply 50 is provided continuously; otherwise, the pH set control circuit 20d could only be set during two minutes of each hour. Upon release of switch 62, the timer circuit returns to it normal position where 8 is in the position shown in FIG. 4, restoring control by timer circuit 20n as previously explained.

It can be appreciated that any desired interval other than one hour may be employed, and any enabling signal period, other than two minutes, may be employed as desired or required.

The foregoing disclosure and description of the invention are illustrative and explanatory thereof, and various changes in the size, shape and materials, as well as in the details of the illustrated construction may be made without departing from the spirit of the invention.

What is claimed is:

1. A sample flow cell for monitoring the halogen and pH level in a flowing liquid stream including:
   a. a hollow closed housing formed of clear material;
   b. said housing having a first inlet opening for the flowing liquid stream on one side of said housing;
   c. said housing having an outlet opening for the flowing liquid stream at the top of said housing;
   d. said housing having a second inlet opening for acid at the bottom of said housing;
   e. said housing having a pair of additional openings through which halogenic and pH sensing probes are positioned to terminate within said housing between the outlet and second inlet openings said first and second inlet openings and said probes being arranged in said housing such that the acid conducted into the bottom of the housing is mixed with the flowing liquid stream and contacts and cleans the probes before discharging out the top of the housing.

* * * * *